(12) United States Patent
Ishikawa et al.

(10) Patent No.: US 6,179,769 B1
(45) Date of Patent: Jan. 30, 2001

(54) MAGNETIC STIMULUS TYPE URINARY INCONTINENCE TREATMENT APPARATUS

(75) Inventors: Norio Ishikawa, Kawasaki; Shin Suda, Tokyo; Tadashi Sasaki, Iruma; Hidehiro Hosaka, Sayama, all of (JP)

(73) Assignee: Nihon Kohden Corporation, Tokyo (JP)

( * ) Notice: Under 35 U.S.C. 154(b), the term of this patent shall be extended for 0 days.

(21) Appl. No.: 08/996,541

(22) Filed: Dec. 23, 1997

(30) Foreign Application Priority Data

Dec. 27, 1996 (JP) .................................................. 8-356794

(51) Int. Cl.[7] .................................. A61N 2/00; A61F 2/00
(52) U.S. Cl. .................................. 600/9; 600/15; 600/29; 128/DIG. 25
(58) Field of Search .............................. 600/9–15, 29–32; 128/DIG. 25

(56) References Cited

U.S. PATENT DOCUMENTS 5,061,234 * 10/1991 Chaney .

5,725,471 * 3/1998 Davey et al. ........................ 600/13

FOREIGN PATENT DOCUMENTS

| 3721864 A1 | | 1/1989 | (DE) . |
| 39 37 793 A1 | * | 5/1991 | (DE) . |
| 93 00 499 | * | 5/1993 | (DE) . |
| 0 501 048 A1 | | 9/1992 | (EP) . |
| WO 94/13357 | * | 6/1994 | (WO) . |
| WO 95/21655 | * | 8/1995 | (WO) . |
| WO 95/27533 | * | 10/1995 | (WO) . |

* cited by examiner

Primary Examiner—John P. Lacyk
(74) Attorney, Agent, or Firm—Hoffmann & Baron LLP

(57) ABSTRACT

A magnetic stimulus type urinary incontinence treatment coil apparatus for generating flux for generating eddy current in a physiological body by providing a coil having an upper surface curved in a concave manner at least in a longitudinal direction such that the coil is fitted to at least part of an area from a front face region of a urethra opening to a rear face region of an anus, the coil wound around the area; and a support for supporting the coil at a position at which the coil is fitted to a patient.

27 Claims, 15 Drawing Sheets

MAGNETIC STIMULUS TYPE URINARY INCONTINENCE TREATMENT APPARATUS

BACKGROUND OF THE INVENTION

Field of the Invention

The present invention relates to a magnetic stimulus type urinary incontinence treatment apparatus for magnetically treating a patient for urinary incontinence by supplying pulse current and thereby generating flux for generating eddy current in a physiological body.

As a urinary incontinence treatment, an electrical stimulus treatment for stress incontinence, urge incontinence and the like by fitting a stimulus electrode to a physiological body and supplying electrical pulses thereto has been well known in addition to a medical treatment and the like. In case of the electrical stimulus treatment, a plug-shaped electrode having a diameter of 2 cm and a length of 4 cm for a vagina or double enveloping electrode having the same dimensions for an anus connected to a pulse wave generator is inserted into the vagina or anus, and pulse current of a repeated frequency of several Hz to several tens Hz, a peak current of 1 to 100 mA and a pulse width of 100 μs to 1 ms is applied directly from the body surface. By so doing, pelvic floor muscle is stimulated and trained by the pulse current applied from the body surface and the weaken muscle is reinforced to thereby strengthen the force for tightening a urethra. Thus, it is effective in the treatment for stress incontinence.

As for urge incontinence caused by the involuntary contraction of a urinary bladder, pudendal nerves or their branches formed from the second to fourth sacral nerves of lunbosacral plexus are stimulated to thereby reflexively prevent the involuntary contraction of the urinary bladder, whereby urinary incontinence can be prevented.

However, the above-stated electrical stimulus treatment using a plug-type electrode requires inserting the electrode into the vagina or anus every time the treatment is conducted. Due to this, there occur problems such as a patient refuses treatment or refuses to continue treatment. Furthermore, if stimulus current is increased so as to obtain a prompt effect in a short period time, there is a possibility that this gives rise to a pain or, what is worse, a burn.

In these circumstances, the present applicant proposed a urinary incontinence treatment apparatus wherein a magnetic stimulus coil for generating repeated pulse-like flux provided at a coil installation tool installed in a room are fitted to regions from the patient's waist to crural region and the flux applied into the body allows eddy current to stimulate pelvic floor muscle, pudendal nerves and the like, as disclosed in the U.S. patent application Ser. No. 08,800,709.

This has made it possible to realize a urinary incontinence treatment apparatus capable of treating a patient for a disease without giving pain to the patient in a non-invasion manner while the patient has his or her clothes on. Meanwhile, in such a treatment, it is necessary to give consideration to electrical power efficiency and, in some cases, to provide a forced cooling system for forcedly cooling a magnetic stimulus coil to supply high current to the coil. Moreover, it is preferable that regions such as a womb, an ovary, a urinary bladder, testicles, which are not directly relevant to the treatment are not stimulated.

SUMMARY OF THE INVENTION

In view of the above respects, it is therefore an object of the present invention to provide a magnetic stimulus type urinary incontinence treatment coil apparatus capable of stimulating regions effective for the urinary incontinence treatment in a concentrated manner.

To obtain the object, according to the present invention, the magnetic stimulus type urinary incontinence treatment coil apparatus generates flux for generating eddy current in a physiological body by comprising a foil having at least an upper surface curved in a concave manner in a longitudinal direction such that the coil is wound along and fitted to at least part of a region from an upper face region of a female patient's urethra opening to a rear face of her anus; and a support for supporting the coil to a position at which the coil is fitted to the patient.

Due to the upper surface having a corresponding concave curved shape, the coil is closely attached to or comes in at least close contact with at least part of the region from an upper face region positioned in front of the urethra opening to a rear face region positioned in the back of the anus. By so doing, eddy current due to flux is generated at a position outside of the patient's body close to a magnetic stimulus target region while the front and rear coil portions approach each other from the same plane in the direction in which they face each other.

According to the present invention, the coil is fitted to be closely attached to or comes in close contact with a fitting target position. Therefore, flux is generated while oriented to the stimulus target region and the region can be stimulated with high eddy current generated by strong magnetic field on the coil surface. The region is effectively stimulated while avoiding stimulating irrelevant regions. Treatment without the need to forcedly cooling the coil is also possible.

In addition, to further narrow the flux generation limit to a desired magnetic stimulus target region, the apparatus according to the present invention is characterized by comprising a coil wound around a magnetic core and a support for supporting the magnetic core to a position at which the coil is fitted to the patient and in that the magnetic core is formed such that the front and rear end faces of the coil are fitted to at least pat of a region from a front face region of a female patient's urethra opening to a rear face region of her anus. The end faces of the magnetic core are fitted to be closely attached to or at least come in close contact with at least part of a region from the front face region of the urethra opening to the rear face region of the anus. By so doing, eddy current passing both pelvic floor muscle and pudendal nerves distributing below the pelvic floor muscle or passing only the pudendal nerves is generated by the flux produced in a concentrated manner in the vicinity of end faces serving as magnetic poles positioned outside the patient's body close to the magnetic stimulus target region.

Moreover, according to the present invention, for purposes of allowing positions of front and rear coils to be adjustable in a longitudinal direction independently of each other, a pair of front and rear rotating plates having inner end portions adjacent to each other are rotatably supported by a tip end portion of a support such that positions of the rotating plates are adjusted in a longitudinal direction, respectively, and a pair of front and rear coils wound around surfaces of the rotating plates are provided at the rotating plates, respectively. The upper surface part of the rear coil of the coils of the front rotating plate and an upper surface part of the front coil of the coils of the rear rotating plate are positioned such that the upper surface parts are fitted to at least regions from a front face region of a urethra opening at rotating adjusted positions, and the pair of front and rear coils are supplied with current in directions opposite to each other. While the patient is seated or standing, the coils provided at the pair of rotating plates, respectively are fitted to be closely attached to or at least come in close contact with at least part of a region from the front end region of the urethra opening to the rear face region of the anus by adjusting the pair of rotating plates in the longitudinal direction, independently of each other.

BRIEF DESCRIPTION OF THE DRAWINGS

FIG. 1 shows an air-core type coil apparatus in an embodiment according to the present invention.

FIG. 2 shows a modification of the coil apparatus shown in FIG. 1.

FIG. 4 shows a feeder system for the apparatus of FIG. 3.

FIG. 11 shows a coil fitting type coil apparatus in another embodiment according to the preset invention.

FIG. 14 shows the coil apparatus of FIG. 13.

DETAILED DESCRIPTION OF THE PREFERRED EMBODIMENTS

Figure 1A:
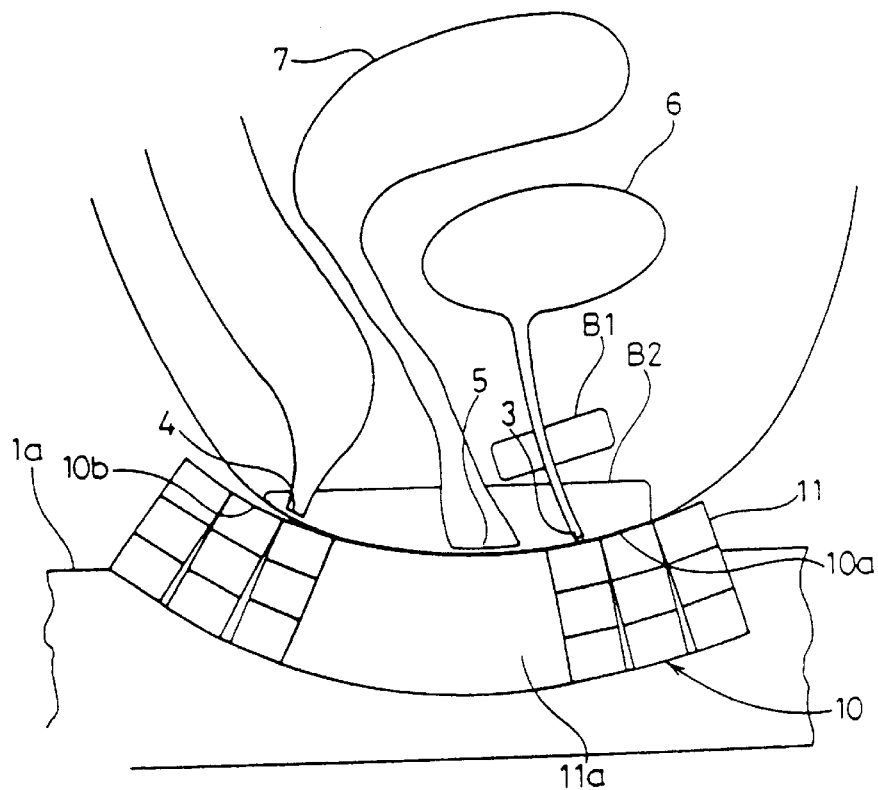
FIG. 1A is a cross-sectional view of the important parts of the apparatus and FIG. 1B is a back view thereof.

Description will be given to a magnetic stimulus type urinary incontinence treatment coil apparatus in an embodiment according to the present invention, with reference to FIGS. 1 through 4. In FIG. 3, reference numeral 9 denotes a urinary incontinence treatment apparatus. The apparatus comprises a feeder system 2 in the back of a chair serving as a support of the apparatus, and a coil 10 provided on a seat 1a.

Figure 1B:
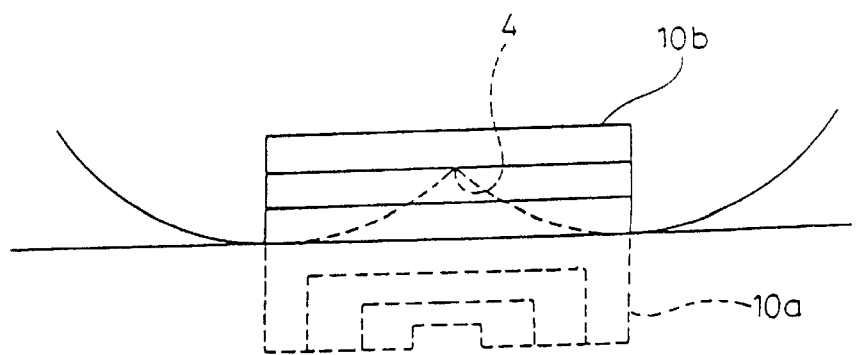

As shown in FIGS. 1A and 1B, the coil consists of three layers formed by rectangularly coiling a rectangular conductor 11 having an insulating material coated film three times along a patient's fitting target region while an air core part 11a is formed at the center. These three layers are connected to one another in parallel and also connected to the feeder system 2. The upper surface is formed to be curved in a concave manner in the longitudinal direction such that a front coil part 10a which is in front of the air core part 11a is fitted along a region of a urethra opening 3 and a rear coil part 10b is fitted along a region of an anus 4. According to the plan view, the coil has a longitudinal width of about 200 mm and a lateral width slightly smaller than the standard gap between joints of both femoral regions to about 100 mm, and the air-core part has a longitudinal width of about 80 mm, a lateral width of about 10 mm and a radius of curvature of about 100 mm. The coil 10 has respective layers connected to one another and is embedded into the seat part 1a serving as a cushion while the coil 10 remains slightly protruding therefrom such that the coil 10 is securely and closely attached to the fitting target region.

Figure 2A:
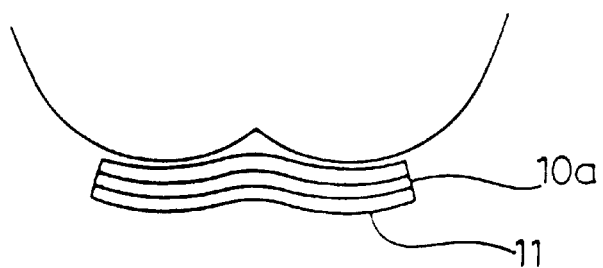
FIG. 2A is a front view and FIG. 2B is a side view of the apparatus.
Figure 2B:
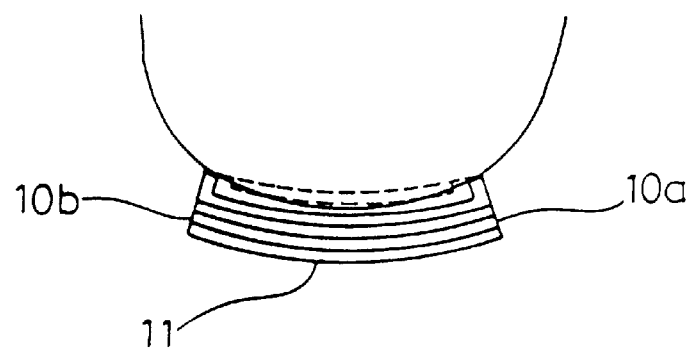
Figure 3:
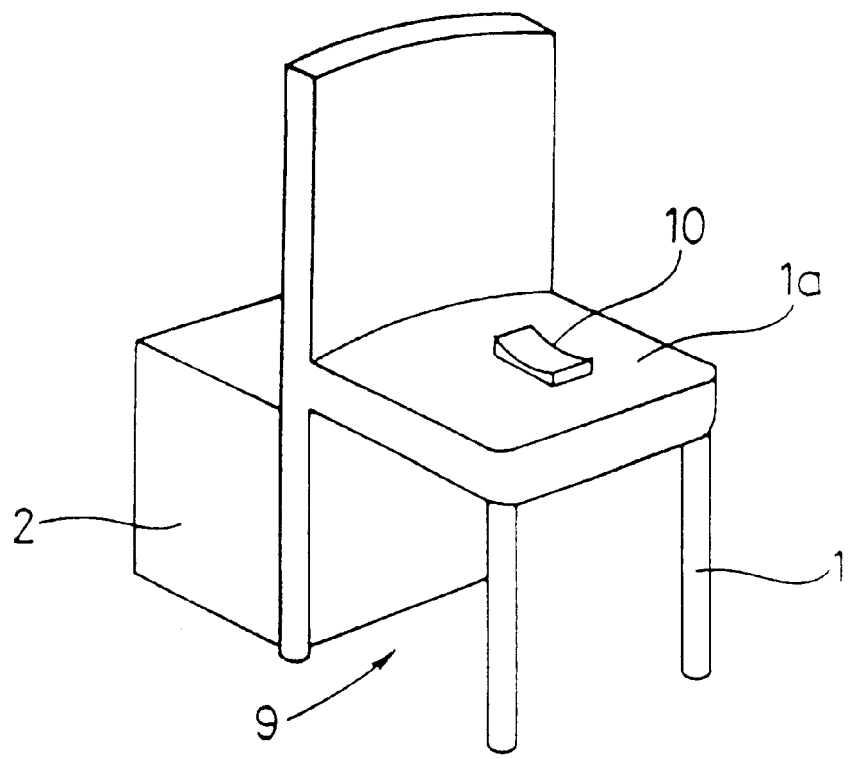
FIG. 3 is a perspective view of a urinary incontinence treatment apparatus employing the coil of FIG. 1.

As shown in FIGS. 2A and 2B, the central portion of the coil 10 in the lateral direction is preferably protuberant in a corrugated manner to ensure closely fitting the coil to the target region. It is possible to protrude the coil 10 higher with smaller width instead of the corrugate shape.

Figure 4A:
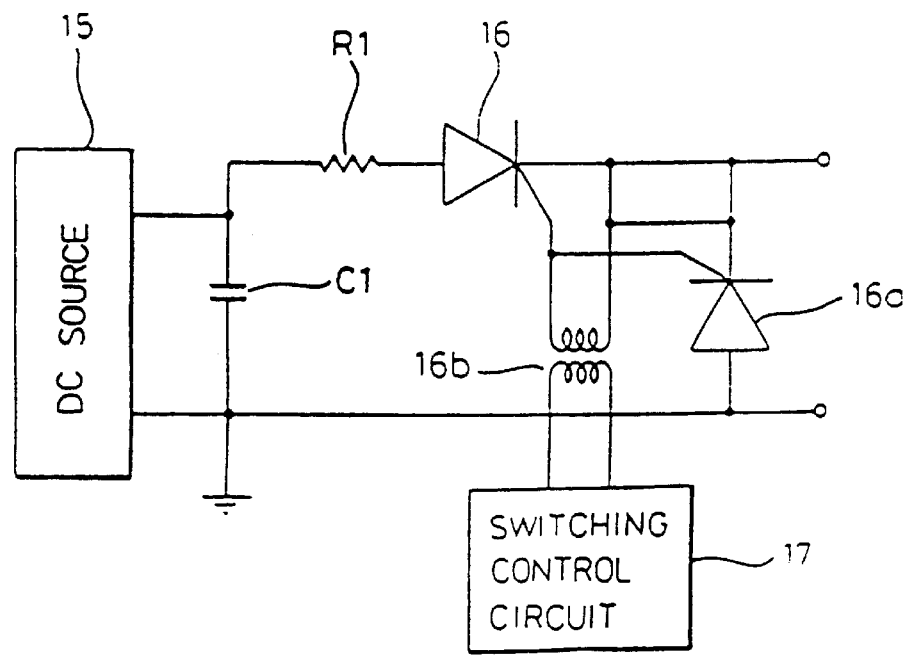
FIG. 4A shows a circuit arrangement of the feeder system and FIG. 4B shows output pulses of the circuit of FIG. 4A.

FIG. 4A shows a circuit arrangement of the feeder system 2. The feeder system 2 consists of a DC power supply 15 capable of adjusting voltage in a range between 100 V to 2 kV, a capacitor C1 of about 300 $\mu$F to be charged by the DC power supply, a thyristor 16 for applying the charging voltage to the coil 10 through a protective resistor R1, a thyristor 16a for absorbing reverse voltage in a switch-off state and a switching control circuit 17 for on-controlling, that is, ignition-controlling these thyristors through a transformer 16b. The repeated frequency of the switching control circuit 17 can be adjusted in a range between 1 Hz and 100 Hz. The winding structure of the coil 10, the voltage of the DC power supply 15 and the capacity of the capacitor C1 allow entire current pulses of about 100 $\mu$s of the coil 10 to generate flux of a flux density of a peak value of about 0.01 to 3 teslas at a maximum of about 3000 A by adjusting voltage.

Figure 4B:
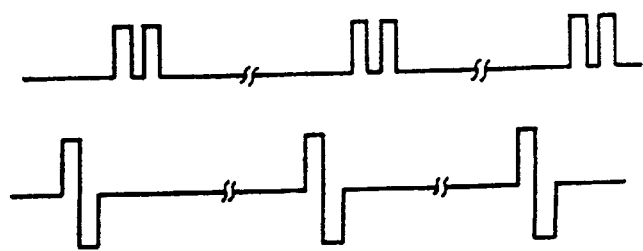

As shown in the upper part of FIG. 4B, at the switching control circuit 17, not only a single pulse but also double pulses of about 100 $\mu$s as stated above can be employed so as not to give pain to the patient as a result of making a pulse wider. Depending on the state and symptom of the stimulus target region of the patient, various pulse stimulus modes can be selected such as a plurality of continuous pulses, bipolar double pulses shown in the lower part of FIG. 4B. The pulse width is not limited to 100 $\mu$s, but can be set to about 1 $\mu$s to 2 ms depending on the state and symptom of the stimulus target region as in the case of the conventional electrical stimulus treatment.

At the time of treatment, as shown in FIG. 1, the patient sits down on the seat part 1a with his or her clothes on. The front coil part 10a slightly protruding at its central portion is fitted to the urethra opening 3 and the rear coil part 10b is fitted to a region of the anus 4. If current is applied in this state, eddy current due to flux is generated at a position outside the patient's body close to magnetic stimulus target regions, that is, the pelvic floor muscle B1 and pudendal nerves B2 distributing into the lower portion of the pelvic floor muscle B1 among the pudendal nerves B2 while the front coil part 10a and the rear coil part 10b, respectively approach each other from the same plane and closely are attached to regions of the urethra opening 3 and anus 4. As a result, the pelvic floor muscle B1, external urethral spincter directly surrounding the urethra, the pudendal nerves B2 and the like are stimulated by ebby current, thus making it possible to effectively conducting treatment for both the urge incontinence and the stress incontinence. The pelvic floor muscle B1 and the pudendal nerves B2 are effectively stimulated without unnecessary gaps provided while avoiding stimulating regions such as a urinary bladder 6, a womb 7, an ovary, testicles and the like which are irrelevant to the treatment. Since the hip region is supported at the seat part 1a, the patient feels it comfortable to sit down on the seat part 1a and does not feel tired. Normally, it is enough to apply electric current to such an extent that no forced cooling is required. If needed, however, it may be set to a maximum of about 200 W on condition of cooling the coil.

Figure 5:
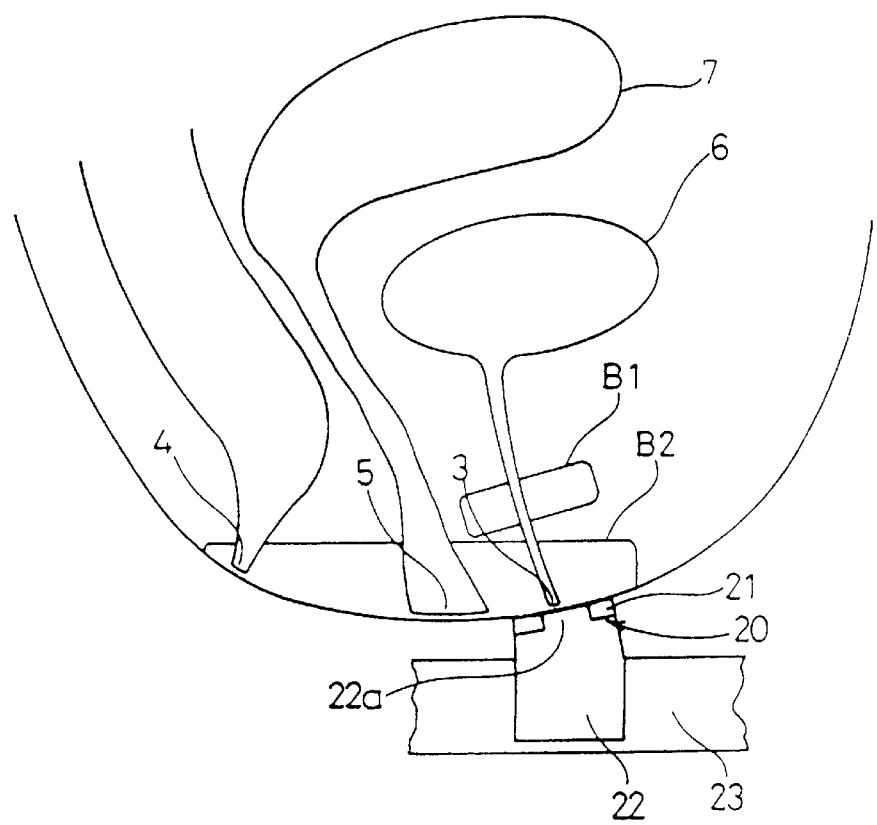
FIG. 5 is a cross-sectional view of the important parts of an air-core type coil apparatus in another embodiment according to the present invention.
Figure 6:
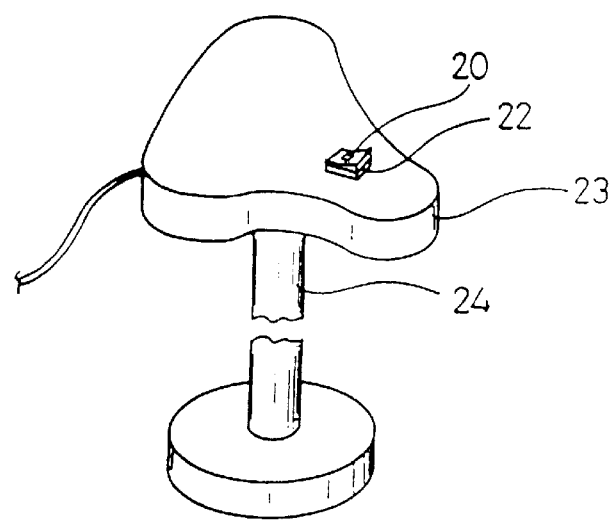
FIG. 6 is a perspective view showing a support of the coil shown in FIG. 5.

FIGS. 5 and 6 show a small size coil apparatus of, again, air core type. A coil 20 is formed to be a closed shape having a longitudinal width of 30 mm and a lateral width of 20 mm according to a plan view. The coil 20 also consists of conductors 21 insulated from each other on both ends facing each other. The air-core part of the coil 20 is fitted into a head part 22a of a coil holding member 22 made of synthetic resin. Upper surfaces of the conductors 21 and the heat part 22a are molded to have convex surfaces corresponding to the urethra 3 and its surrounding surface regions. The coil holding member 22 is slightly protruded from a seat part 23 of bicycle saddle shape installed on the tip end portion of a stand 24 such that the upper surface of the coil 20 can be securely and closely attached to the surface regions around the urethra opening 3. In this case, the pudendal nerves B2 are mainly stimulated, which is effective against urge incontinence.

Figure 7:
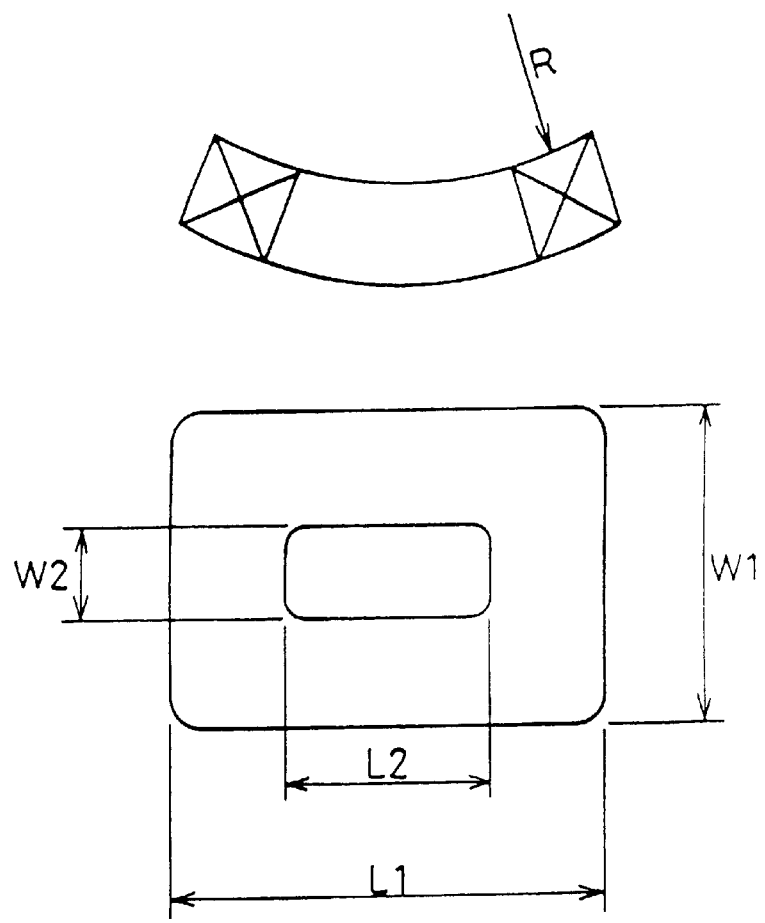
FIG. 7 is a cross-sectional view and a plan view showing the typical shape of the air-core type coil according to the present invention.

FIG. 7 shows a typical shape of coils including the above-stated coil according to the present invention. According to the plan view, the longitudinal width L1 of the outer dimension is 30 to 300 mm and the lateral width W1 is 20 to 120 mm. The longitudinal width L2 of the air core part is 20 to 160 mm and the lateral width W2 thereof is 10 to 40 mm. The radius of curvature R on the upper surface of the coil is 90 to 150 mm. A female patient of large build has a longitudinal width L1 of about 300 mm from an upper face region in front of the urethra opening to a rear face region in the back of the anus, and has a lateral width W1 of a maximum of about 120 mm corresponding to the gap between joints of the both femoral regions. The larger the shape, that is, the larger the inner dimension of the air-core part is, the deeper from the body surface the eddy current can be generated and the shape or inner dimension is specified by a width of a conductor with respect to its outer dimension. By using such a coil, the highest eddy current is flown though a region right on the coiled conductor. However, the upper surface is not necessarily completely arc shaped. It can precisely correspond to the shape of the fitting target region and, in some cases, may be slightly curved in the lateral direction. The curved shape of the coil can be provided by molding the surface of the conductor, or by coiling a plurality of conductors along curved surfaces. Furthermore, the shape of the coil is not limited to rectangular. It may be circular, ellipsoidal and the like depending on the stimulus target region.

Figure 8:
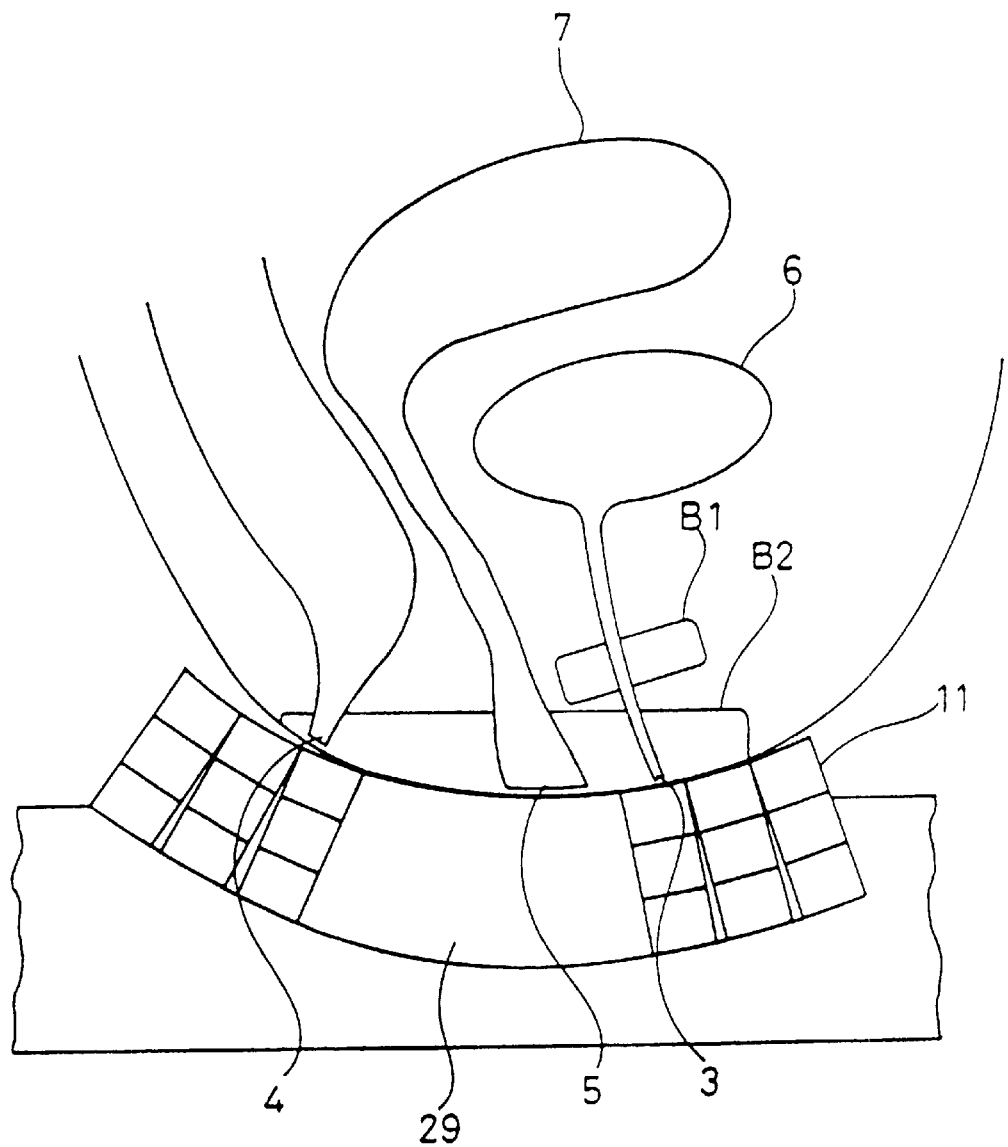
FIG. 8 is a cross-sectional view of the important parts of the coil apparatus having a magnetic core installed at the air-core part of the air-core type coil of FIG. 1.

FIG. 8 shows a coil apparatus wherein a magnetic core 29, such as a ferrite core, having good frequency characteristics and low loss is fitted into the air-core part 11a of the coil 10 shown in FIG. 1. In this case, by shallowly concentrating a flux generation region into a central portion, the pudendal nerves B2 are mainly stimulated in a concentrated manner while the flux hardly arrives at the pelvic floor muscle B1. This is especially effective in the treatment for urge incontinence and it can greatly prevent regions irrelevant to the treatment from being stimulated.

Figure 9:
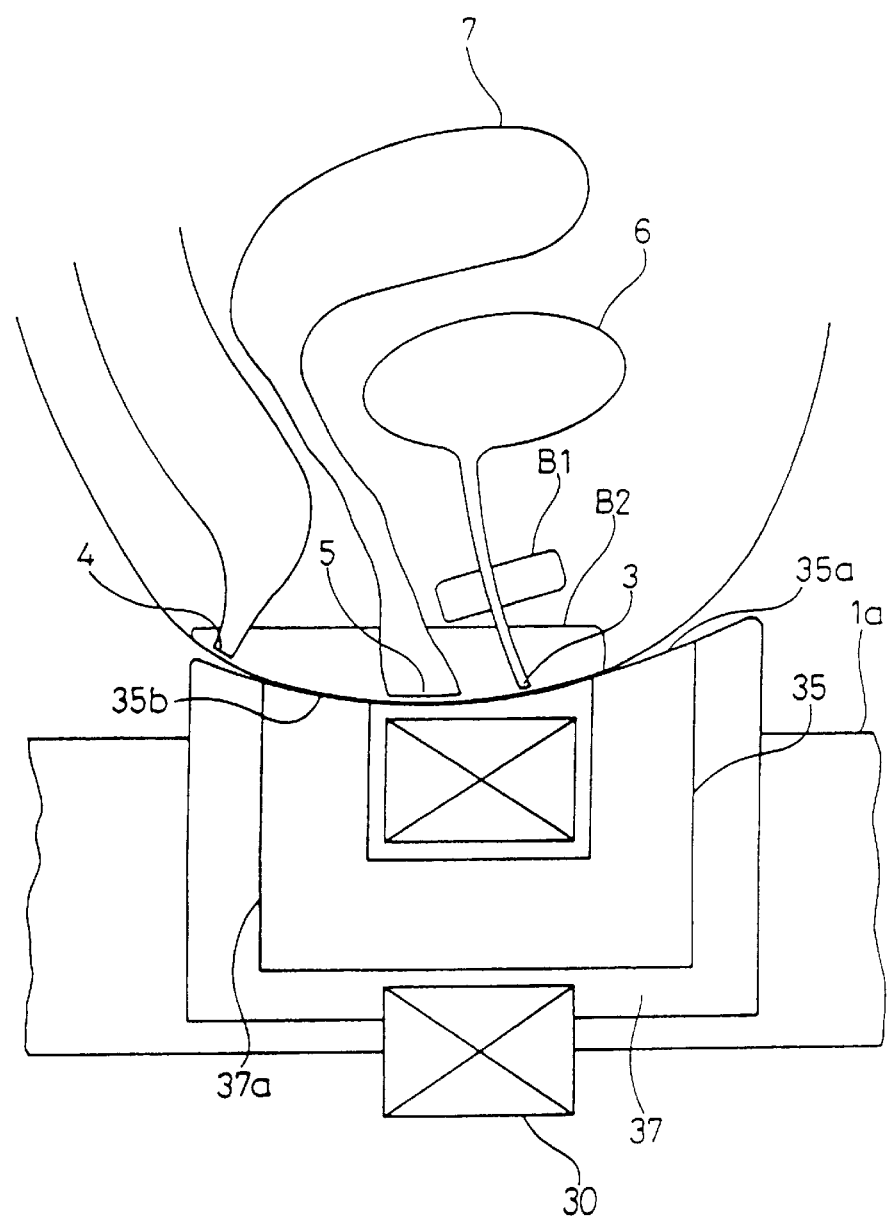
FIG. 9 is a cross-sectional view of the important parts of a coil having with one magnetic core in an embodiment according to the preset invention.
Figure 10:
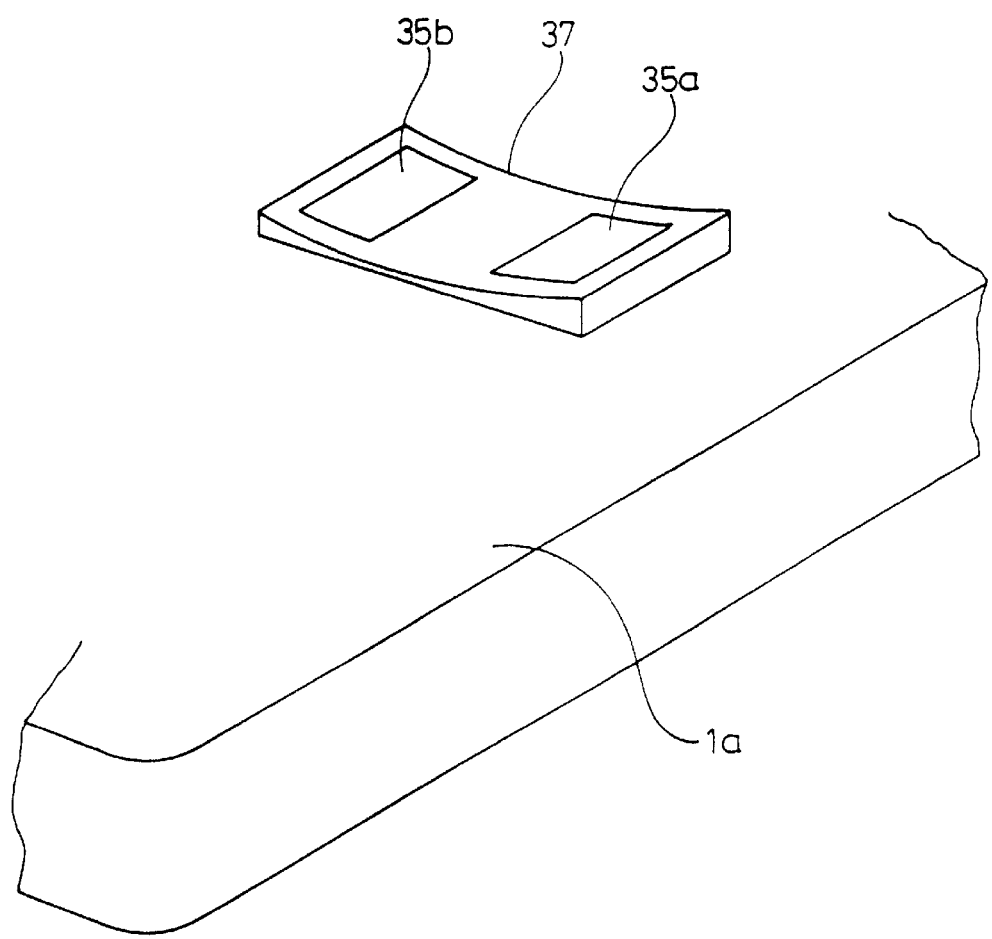
FIG. 10 is a perspective view showing part of a support of the coil shown in FIG. 9.

FIG. 9 shows a magnetic core fitting type coil apparatus for fitting a magnetic core to a patient. A front end face 35a serving as one magnetic pole of a U-shaped magnetic core 35 around which a coil 30 is wound is located at a slightly upper position than a rear end face 35b serving as the other magnetic pole thereof and upper surfaces thereof are formed to be concave curved such that the front end face 35a is fitted to a front face region of the female patient's urethra opening 3 and the rear end face 35b is fitted to a rear face region of the patient's clitoris. The magnetic core 35 is fitted into a concave portion 37a of a holding member 37 made of synthetic resin and having an upper surface slightly concave-curved. As shown in FIG. 10, the holding member 37 is installed on the seat part 1a such that the end faces 35a and 35b are slightly protruded from the above-mentioned seat part 1a, and the lower end portion of the coil 30 is exposed to be air-cooled. By so doing, the arch like flux can be generated between the end faces 35a and 35b in a convergent manner to thereby stimulate both the pelvic floor muscle B1 and the pudendal nerves B2. Since the flux can be generated in an effectively convergent manner, power consumption can be greatly reduced.

Figure 11A:
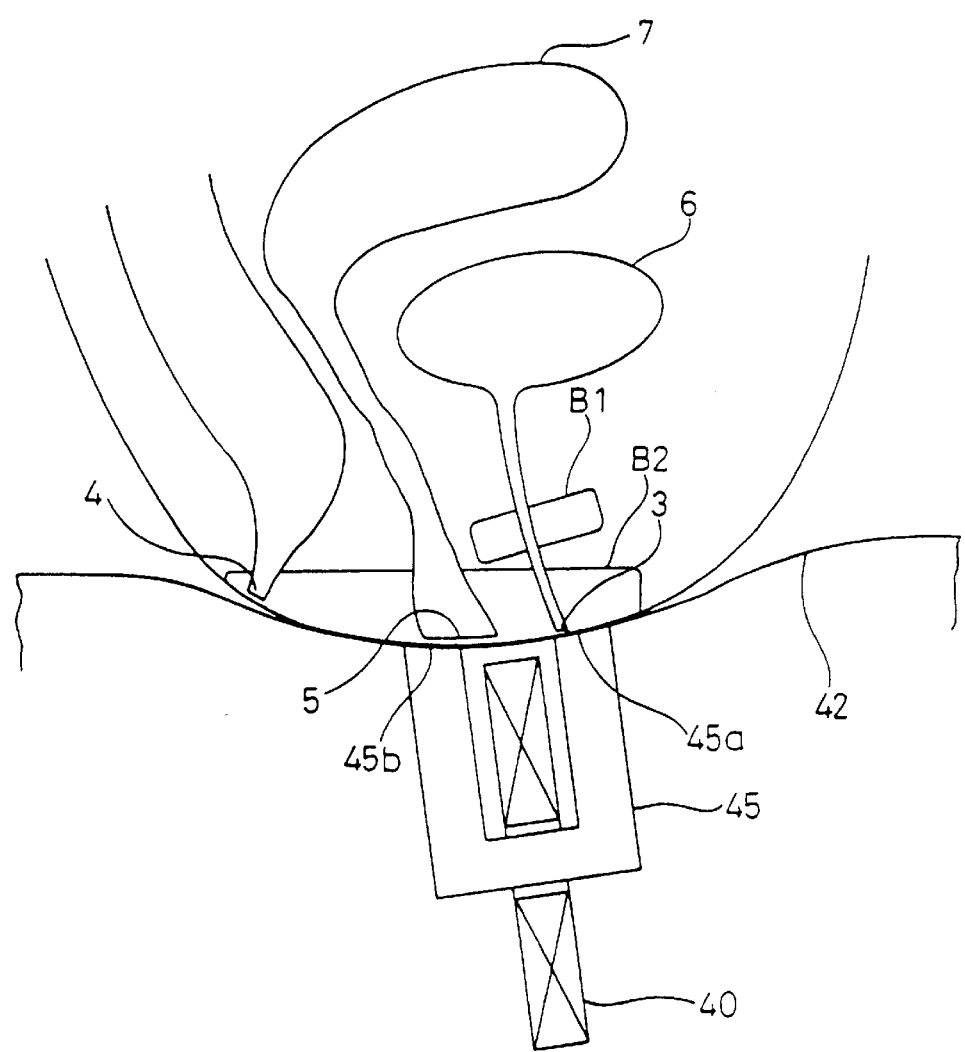
FIG. 11A is a cross-sectional view of the apparatus with one coil and FIG. 11B is a cross-sectional view of the apparatus with two coils.

FIG. 11A shows a coil apparatus of, again, magnetic core fitting type. A front end face 45a of a U-shaped magnetic core 45 around which a coil 40 is wound, is located at a slightly upper position than a rear end face 45b and upper surfaces thereof are formed to be concave-curved such that the front end face 45a is fitted to a region of the female patient's urethra opening 3 and the rear end face 45b is fitted to a region of a clitoris 5. The portion between the end faces 45a and 45b is molded and the surfaces thereof are formed on corresponding curved surface, respectively. The magnetic core 45 is embedded into a seat part 42 of a chair or stand having a central portion in the longitudinal direction curved to be of corresponding concave shape. In this case, the end faces 45a and 45b serving as magnetic poles are fitted to come in close contact with a fitting target region. Since the distance between the end faces 45a and 45b is short, the flux does hardly reach the pelvic floor muscle B1 and mainly stimulates the pudendal nerves B2.

Figure 11B:
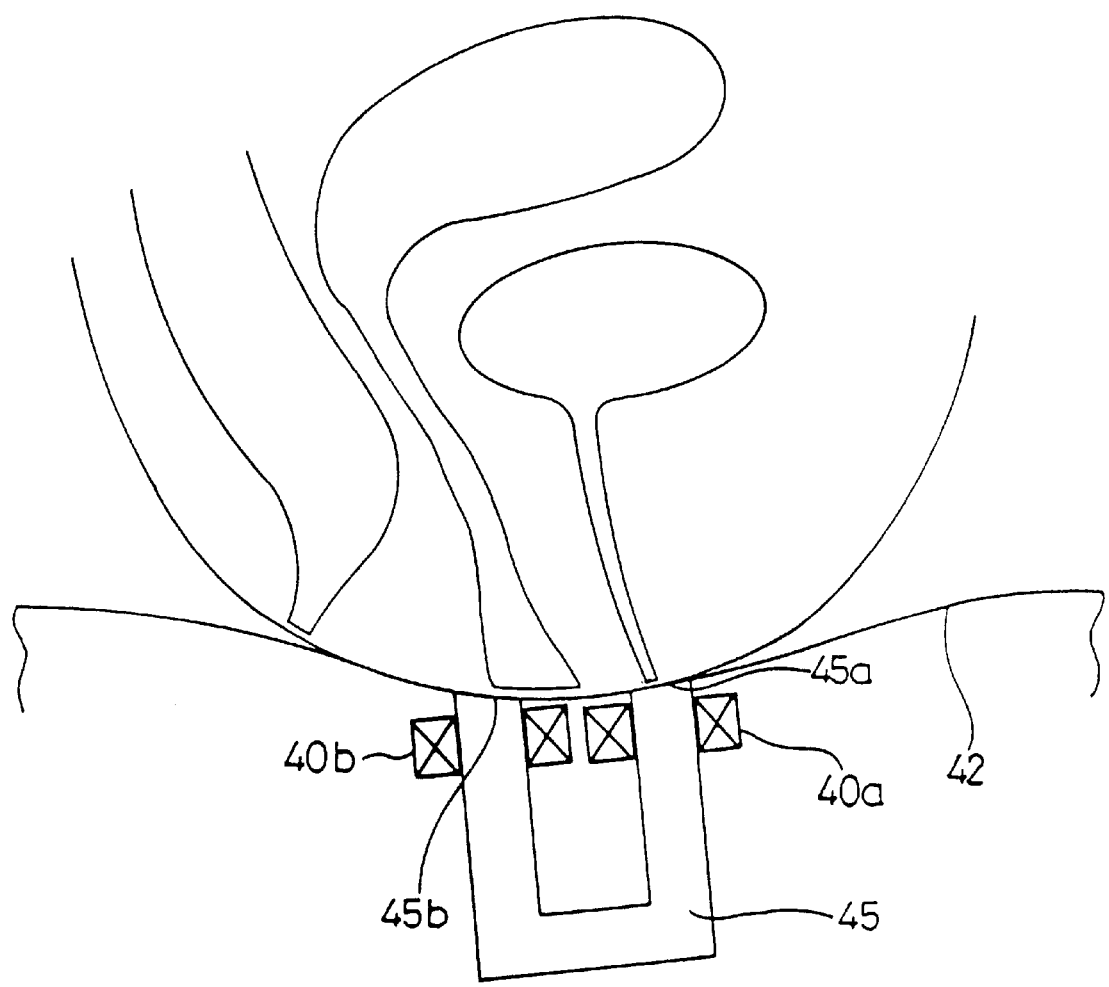

In FIG. 11B, the coil 40 includes two coil parts 40a and 40b. The coil parts 40a and 40b are wound in the vicinity of the end faces 45a and 45b of the U-shaped magnetic core 45 positioned in the vicinity of the female patient's urethra opening 3 and the clitoris 5, respectively and current is supplied to the coil parts 40a and 40b, respectively such that the flux of the coil parts 40a and 40b flows through the magnetic core 45 in the same direction.

Figure 11C:
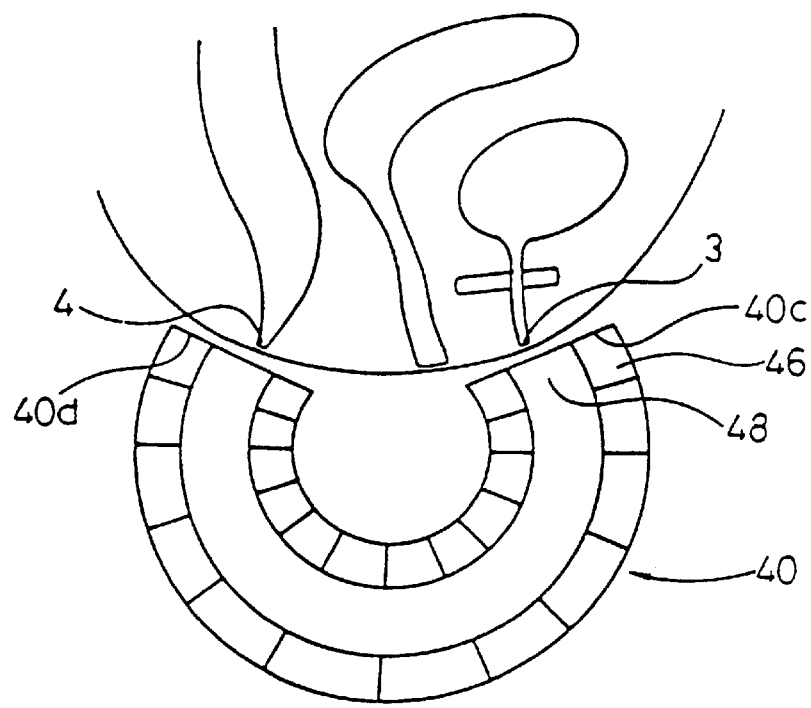
FIG. 11C is a cross-sectional view of a coil which is a modified version of the coil of FIG. 11A or FIG. 11B.
Figure 11D:
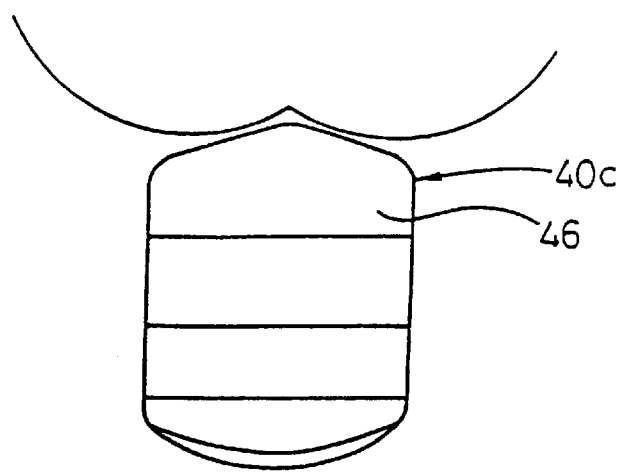
FIG. 11D is a front view of the coil shown in FIG. 11C.

As shown in FIG. 11C, the coil 40 consists of a conductor 46 coiled once to be U-shaped. The coil 40 comprises a front coil part 40c surrounding vicinity of the urethra opening 3 by forming an air-core part 48 and a rear coil part 40d surrounding the vicinity of the anus 4 by forming an air-core part 48. The central portion of the conductor of these coil parts are protuberant in the lateral direction as shown in FIG. 11D. It is possible to install a common U-shaped magnetic core at the air-core part 48 of the conductor 46. Alternatively, the coil 40 can be continuously wound by one conductive line.

Figure 12:
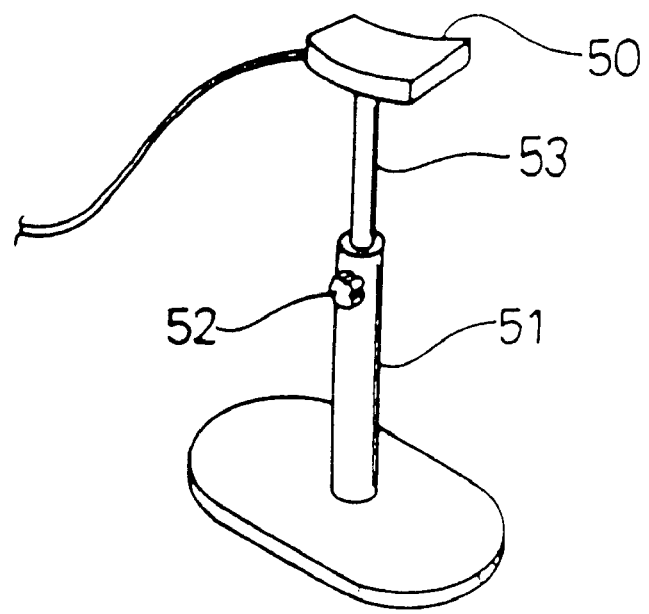
FIG. 12 is a perspective view of a support in another embodiment according to the present invention.

FIG. 12 shows a stand type coil support. A pipe 51 of the support slidably supports a rod having a coil 50 with an air core or a magnetic core installed on a tip end portion thereof. The position of the coil 50 can be locked to a position slidably adjusted by a thumbscrew 52. The support enables the coil 50 to be fitted to a patient who remain standing while adjusting the position of the coil 50 as required.

Figure 13:
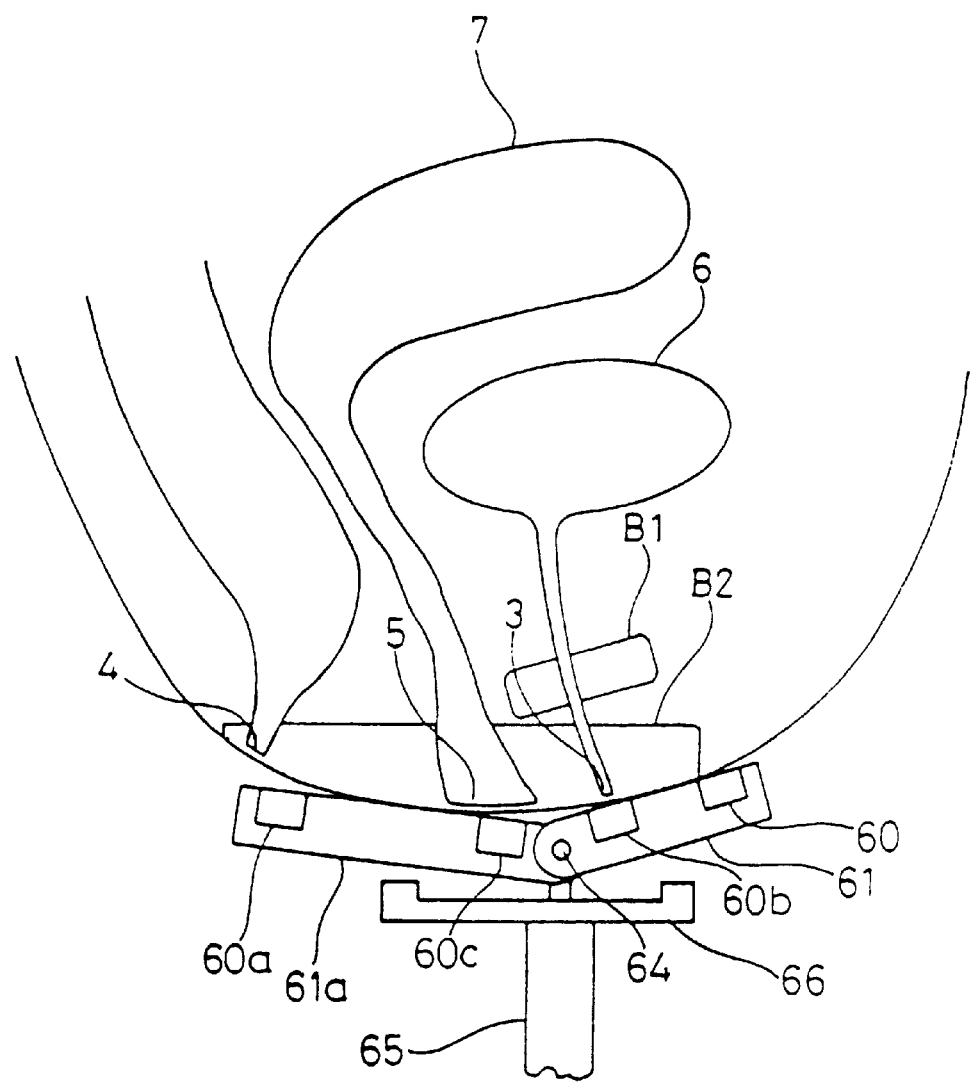
FIG. 13 is a cross-sectional view showing the important parts of the rotatable plate type coil apparatus.
Figure 14A:
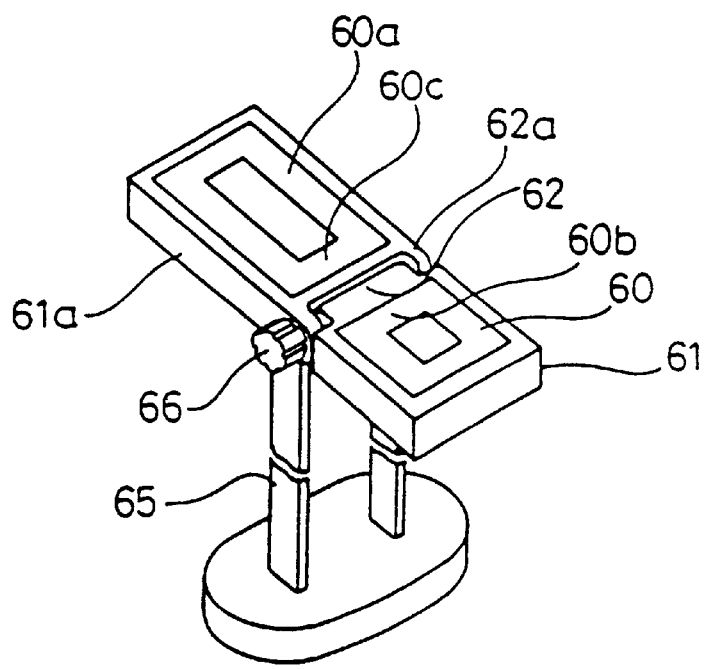
FIG. 14A is a perspective view of the apparatus and FIG. 14B is a cross-sectional view showing part of the apparatus.
Figure 14B:
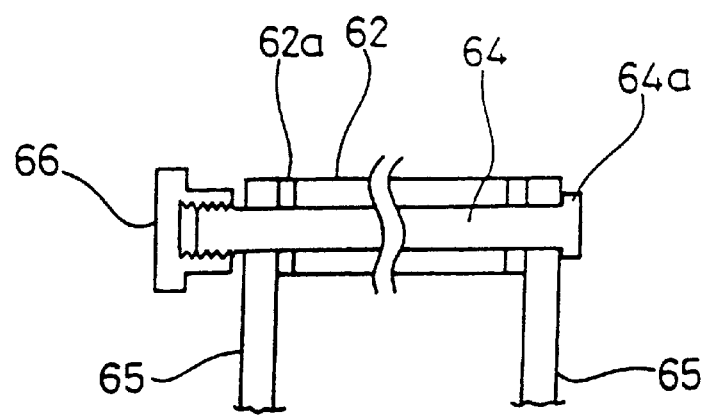

FIGS. 13 and 14 show a rotation type coil apparatus. Complementary-shape protrusion parts 62 and 62a on inner end portions of a pair of rotating plates 61 and 61a into which coils 60 and 60a are embedded, respectively, are rotatably supported by a rotation axis 64 of a stand 65. A thumbscrew 66 is engaged with the rotation axis 64 and the rotating operation allows a flange part 64a on the opposite end of the rotation axis 64 to be secured to the stand 65 and the adjusted position to be locked. Moreover, the stand 65 is provided with a stopper 66 for supporting the rotating plates 61 and 61a in the horizontal direction. The lateral widths of the rotating plates 61 and 61a are set in accordance with the gap between the joints of both femoral regions to, for example, 100 mm.

The coils 60 and 60a are wound around surfaces of the corresponding rotating plates 61 and 61a such that air core parts are formed at central portions, respectively. The coil upper surface portion 60b which is in the rear of the air-core part of the coil 60 on the front side rotating plate 61 and the coil upper surface part 60c which is in front of the air core part of the coil 60a of the rear side rotating plate 61a are positioned such that the coil upper surface part 60b is fitted to a region of a female patient's urethra opening 3 and the coil upper surface part 60c is fitted to a region of the patient's clitoris 5. The coils 60 and 60a are connected such that they are supplied with current flowing opposite directions.

By so doing, the rotation position is adjusted in accordance with the patient's form and the coil upper surface part 60b is fitted to the urethra opening 3 and the coil upper surface part 60c is fitted to the clitoris 5, thereby stimulating mainly the pudendal nerves B2. It is noted here that if the coil upper surface part 60c is deformed to be positioned in a rear face region of the clitoris 5, a flux generation region becomes wider and the pelvic floor muscle can be simultaneously stimulated.

It is also possible to install the rotating plates 61 and 61a on the tip end portion of the stand as shown in FIG. 12 and to provide a coil apparatus capable of treating a patient while the patient remains standing. In that case, the lateral widths of the rotating plates 61 and 61a are set to be slightly smaller than that of the standard gap between the joints of femoral regions. In addition, the rotating plates 61 and 61a are friction-engaged with the rotation axis and held at appropriate adjusted positions so that the structure of the side of the thumbscrew and the like may not be a hindrance to the apparatus.

What is claimed is:

1. A magnetic stimulus type urinary incontinence treatment coil apparatus for magnetically treating a patient for urinary incontinence by applying pulse current and thereby generating flux for generating eddy current in a physiological body, said apparatus comprising:
   a coil having an upper surface curved in a concave manner in a longitudinal direction such that the coil is adapted to be fitted to at least part of an area from a front face region of an urethra opening to a back face region of an anus, said coil being positionable around the area; and
   a support for supporting the coil at a position at which the coil is fitted to the patient.

2. A magnetic stimulus type urinary incontinence treatment coil apparatus according to claim 1, wherein
   a longitudinal width of the coil is 30 to 300 mm and a lateral width of the coil is 20 to 120 mm according to a plan view.

3. A magnetic stimulus type urinary incontinence treatment coil apparatus according to claim 1, wherein a longitudinal width of the coil is about 30 mm and a lateral width of the coil is 20 to 30 mm according to a plan view so as to be adapted to fit the coil to a region in the vicinity of the urethra opening.

4. A magnetic stimulus type urinary incontinence treatment coil apparatus according to claim 1, wherein a longitudinal width of the coil is 200 to 300 mm and a lateral width of the coil is 50 to 120 mm according to a plan view so as to be adapted to fit the coil to a region from the vicinity of the urethra opening to a region of the anus.

5. A magnetic stimulus type urinary incontinence treatment coil apparatus according to claim 1, wherein a magnetic core is provided in an air-core part formed at a central portion around which the coil is wound.

6. A magnetic stimulus type urinary incontinence treatment coil apparatus according to claim 1, wherein the coil is adapted to be fitted to a seat part supported by the support to sit the patient, the coil adapted to protrude from an upper surface of the seat part.

7. A magnetic stimulus type urinary incontinence treatment coil apparatus according to claim 1, wherein the coil is protuberant at a central portion in a lateral direction.

8. A magnetic stimulus type urinary incontinence treatment coil apparatus according to claim 1, wherein the support is a chair put on a floor.

9. A magnetic stimulus type urinary incontinence treatment coil apparatus according to claim 1, wherein the support is a stand put on a floor.

10. A magnetic stimulus type urinary incontinence treatment coil apparatus according to claim 1, wherein the coil consists of a front coil part formed about a first air core part adapted to surround the urethra opening, and a rear coil part formed about a second air core part adapted to surround the vicinity of the anus.

11. A magnetic stimulus type urinary incontinence treatment coil apparatus according to claim 10, wherein a common U-shaped magnetic core is provided in the air core part of the front coil part and the air core part of the rear coil part.

12. A magnetic stimulus type urinary incontinence treatment coil apparatus for magnetically treating a patient for urinary incontinence by applying pulse current and thereby generating flux for generating eddy current in a physiological body, said apparatus comprising:
    a coil wound around a magnetic core; and
    a support for supporting said magnetic core at a position at which the magnetic core is adapted to be fitted to the patient, wherein
    said magnetic core is formed such that a pair of end faces spaced from each other for forming magnetic poles of the magnetic core are adapted to be fitted to at least part of a region from a front face region of a urethra opening to a rear region of an anus and wherein the magnetic core is adapted to be fitted to a seat part supported by the support to sit the patient such that the end faces are adapted to protrude from the upper surface of the seat part.

13. A magnetic stimulus type urinary incontinence treatment coil apparatus according to claim 12, wherein the magnetic core is formed such that the front end face is adapted to be fitted to a region in the vicinity of the urethra opening and the rear end face is adapted to be fitted to a clitoris region, and that said front end face is located at a slightly upper position than that of said rear end face.

14. A magnetic stimulus type urinary incontinence treatment coil apparatus according to claim 12, wherein the magnetic core is formed such that the front end face is adapted to be fitted to a front face region of the urethra opening and the rear end face is adapted to be fitted to a rear face region of the clitoris, and that said front end face is located at a slightly upper position than that of said rear end face.

15. A magnetic stimulus type urinary incontinence treatment coil apparatus for magnetically treating a patient for urinary incontinence by applying pulse current and thereby generating flux for generating eddy current in a physiological body, said apparatus comprising:

a front and rear rotating plates having inner end portions adjacent to each other and rotatably supported by a tip end portion of a support such that positions of the rotating plates are adjusted in a longitudinal direction; and a first coil wound around a surface of the front rotating plate and a second coil wound around a surface of the rear rotating plate, and wherein an upper surface part of said first coil of said front rotating plate and an upper surface part of said second coil of said rear rotating plate are positioned such that said first and second coil upper surface parts are adapted to be fitted to at least regions from a front face region of a urethra opening to an anus region at rotating adjusted positions, and said first and second coils are supplied with current flowing in directions opposite to each other.

16. A magnetic stimulus type coil apparatus for magnetically treating a patient comprising:

a coil having at least an upper surface curved in a concave manner in a longitudinal direction such that said coil is adapted to be fitted to a region of a physiological body to be treated.

17. The magnetic stimulus type coil apparatus according to claim 16, further comprising:

a support for supporting said coil, said coil is adapted to be fitted to a seat part supported by said support to sit the patient and adapted to protrude from an upper surface of said seat part.

18. The magnetic stimulus type coil apparatus according to claim 16, wherein said coil has a central portion which protrudes toward the physiological body in a lateral direction.

19. The magnetic stimulus type coil apparatus according to claim 16, wherein said coil consists of a front coil part formed about a front core part and a rear coil part formed around a rear core part.

20. The magnetic stimulus type coil apparatus according to claim 19, wherein a common U-shaped magnetic core is provided in the core part of said front coil part and the core part of said rear coil part.

21. A magnetic stimulus type coil apparatus for magnetically treating a patient comprising:

a coil wound around a magnetic core; and a support for supporting said magnetic core at a position at which said magnetic core is adapted to be fitted to the patient, wherein said magnetic core is formed such that a pair of end faces spaced from each other for forming magnetic poles of said magnetic core are adapted to be fitted to a region of a physiological body to be treated and said magnetic core is adapted to be fitted to a seat part supported by said support to sit the patient such that said end faces are adapted to protrude from the upper surfaces of the seat part.

22. A magnetic stimulus type coil apparatus for magnetically treating a patient comprising:

a front and rear rotating plates having inner end portions adjacent to each other and rotatably supported by a tip end portion of a support such that positions of said rotating plates are adjusted in a longitudinal direction; and a first coil wound around a surface of said front rotating plate and a second coil wound around a surface of said rear rotating plate, and wherein an upper surface part of said first coil of said front rotating plate and an upper surface part of said second coil of said rear rotating plate are positioned such that said first and second coil upper surface parts are adapted to be fitted to a region of a physiological body to be treated, and said first and second coils are supplied with current flowing in directions opposite to each other.

23. A magnetic stimulus type urinary incontinence treatment coil apparatus for magnetically treating a patient for urinary incontinence by applying pulse current and thereby generating flux for generating eddy current in a physiological body, said apparatus comprising:

a coil having an air core formed at a center and having an upper surface curved in a concave manner in a longitudinal direction such that the coil is adapted to be fitted to an area from a front face region of an urethra opening to a back face region posterior to the urethra, said coil being positioned around the area; and a support for supporting the coil at a position at which the coil is fitted to the patient.

24. A magnetic stimulus type coil apparatus for magnetically treating a patient comprising:

a coil wound around a magnetic core; and a support for supporting said magnetic core at a position at which said magnetic core is adapted to be fitted to the patient, wherein said magnetic core having a first and a second spaced end faces for forming magnetic poles of said magnetic core, said first and second end faces having a concave shape of such a degree to permit said first and second end faces to accommodate contours of a region of a physiological body to be treated and be fitted substantially directly to the region.

25. A magnetic stimulus type coil apparatus for magnetically treating a patient comprising:

a coil having an upper surface curved in a convex manner in a longitudinal direction such that said coil is adapted to be fitted to a region of a physiological body to be treated; and a support for supporting said coil, said coil is adapted to be fitted to a seat part supported by said support to sit the patient and adapted to protrude from an upper surface of said seat part.

26. A magnetic stimulus type coil apparatus for magnetically treating a patient comprising:

a coil having an upper surface curved in a convex manner in a longitudinal direction such that said coil is adapted to be fitted to a region of a physiological body to be treated, and wherein said coil has a central portion which protrudes toward the physiological body in a lateral direction.

27. A magnetic stimulus type coil apparatus for magnetically treating a patient comprising:

a coil having an upper surface curved in a convex manner in a longitudinal direction such that said coil is adapted to be fitted to a region of a physiological body to be treated, and said coil consists of a front coil part formed about a front core part and a rear coil part formed around a rear core part, and a common U-shaped magnetic core being provided in the core part of said front coil part and the core part of said rear coil part.

* * * * *